US005558812A

United States Patent [19]
Hahn et al.

[11] Patent Number: 5,558,812
[45] Date of Patent: Sep. 24, 1996

[54] LIQUID ENZYME FORMULATIONS

[75] Inventors: Wilfried Hahn; Hubert Herrman; Torsten Kiesser, all of Nienburg; Vera Sander, Garbsen, all of Germany

[73] Assignee: Solvay Enzymes GmbH & Co. KG., Neinburg/Weser, Germany

[21] Appl. No.: 257,826

[22] Filed: Jun. 9, 1994

[30] Foreign Application Priority Data

Jun. 16, 1993 [DE] Germany .......................... 43 19 908.9

[51] Int. Cl.$^6$ ................................ C12N 9/00; C11D 7/00

[52] U.S. Cl. .......................... 510/321; 435/187; 435/188; 435/263; 435/264; 510/300; 510/303; 510/363; 510/370; 510/393; 510/418

[58] Field of Search .................................... 435/183, 187, 435/212, 263, 264, 188; 252/544, 174, 174.12, 174.21, Dig. 2, Dig. 14, Dig. 12

[56] References Cited

U.S. PATENT DOCUMENTS

| | | | |
|---|---|---|---|
| 3,553,139 | 1/1971 | McCarthy | 252/95 |
| 3,717,550 | 2/1973 | Zifter | 195/63 |
| 3,950,277 | 4/1976 | Stewart et al. | 252/541 |

FOREIGN PATENT DOCUMENTS

| | | |
|---|---|---|
| 286181 | 1/1991 | German Dem. Rep. . |

OTHER PUBLICATIONS

Derwent Abstract of JP–A 4/065, 494 (Kao Corp.) Mar. 1992.

Derwent Abstract of RD 337,091 (Novo–Nordisk AS) May 1992.

*Primary Examiner*—Margaret Einsmann
*Attorney, Agent, or Firm*—Evenson, McKeown, Edwards & Lenahan

[57] ABSTRACT

Liquid enzyme formulations which contain the enzyme in the form of aqueous enzyme particle suspension, colloidal fillers and a liquid alkylene oxide polymer based on ethylenediamine and having a molecular weight in the range from 500 to 8200. The liquid enzyme formulations of the invention may contain any enzyme customarily incorporated in detergents or used for cleaning purposes, especially alkaline proteases. Processes for preparing such liquid enzyme formulations and for using them in liquid detergents and/or cleaners are also disclosed.

12 Claims, No Drawings

LIQUID ENZYME FORMULATIONS

BACKGROUND OF THE INVENTION

The present invention relates to liquid enzyme formulations, to a process for their preparation and to their use in liquid detergent and cleaner compositions.

Enzymes are employed to increase the washing activity in numerous liquid detergent and cleaner compositions, for example for cleaning textiles or crockery. Enzymes normally used for this purpose include proteases, lipases, amylases and/or cellulases. In this regard, there is a danger that the other detergent ingredients, which are present in the liquid detergent or cleaning composition, may adversely affect the stability of the enzyme.

Another frequent problem with conventional enzyme-containing liquid compositions is inadequate sedimentation stability.

There is also a need for liquid enzyme formulations which can be processed satisfactorily into liquid detergent and cleaner compositions with high enzyme stability.

SUMMARY OF THE INVENTION

It is therefore the object of the invention to provide improved liquid enzyme formulations which can be readily processed into liquid detergent or cleaner compositions.

Another object of the invention it to provide liquid enzyme formulations with improved stability against sedimentation.

A further object of the invention is to provide liquid enzyme formulations with improved enzyme stability.

These and other objects of the invention are achieved by providing a liquid enzyme formulation comprising 3 to 25 wt-% of suspended enzyme particles, 1 to 10 wt-% of a colloidal filler, and 65 to 95.5 wt-% of a liquid alkylene oxide polymer of ethylenediamine having a molecular weight in the range from 500 to 8200.

DETAILED DESCRIPTION OF PREFERRED EMBODIMENTS

The present invention provides liquid enzyme formulations which are sedimentation-stable and have a high enzyme stability and are therefore very suitable for use in liquid detergent and cleaner compositions.

The invention thus relates to a liquid enzyme formulation which contains 3 to 25% by weight of suspended enzyme particles, optionally 0.5 to 30% by weight of water, 1 to 10% by weight of a colloidal filler and 65 to 95.5% by weight of a liquid alkylene oxide polymer based on ethylenediamine with a molecular weight in the range from 500 to 8200.

The liquid enzyme formulations according to the invention may contain any of the enzymes customarily used in detergent and cleaner compositions, for example proteases, lipases, amylases, glucanases such as cellulases, hemicellulases, oxidases or oxygenases. The formulations of the invention may contain only a single enzyme or they may contain a mixture of two or more enzymes, for example a protease/amylase mixture or protease/lipase mixture. The liquid enzyme formulations according to the invention preferably contain proteases and/or amylases.

If the liquid enzyme formulations according to the invention contain an amylase, it is advantageously a thermostable amylase such as, for example, Optitherm™.

In a particularly preferred embodiment, the liquid enzyme formulations according to the invention contain proteases, especially alkaline proteases. Particularly advantageous alkaline proteases are the so-called subtilisins. Subtilisins are alkaline proteases with a pH optimum in the alkaline pH range and an essential serine residue in the active center. In this regard, it is also possible to advantageously employ optimized proteases which have improved properties such as increased washing efficiency or improved stability as a result of known biotechnological mutagenesis. Proteases can be obtained in a known manner from Gram-positive bacteria or fungi. The preferred proteases are those obtained from bacillus strains, for example subtilisins such as subtilisin BPN', subtilisin Carlsberg and proteases which can be isolated from *Bacillus subtilis, Bacillus amyloliquefaciens, Bacillus licheniformis, Bacillus lentus, Bacillus mesentericus* or *Bacillus alcalophilus.* Particularly preferred proteases have a pH optimum in the range from pH 7 to pH 13 and are commercially available, for example, as Savinase™, Maxacal™, Durazym™, Maxapem™ or Opticlean™.

The enzymes suitable for the liquid enzyme formulations according to the invention can be obtained in a known manner by fermentation processes from suitable microorganisms, in particular from bacteria or fungi. The fermenter broths produced in the fermentation are freed of insoluble accompanying substances, for example by filtration, and subsequently concentrated in a known manner, for example by membrane filtration processes or by thin film evaporation, resulting in so-called enzyme concentrates which normally contain the enzyme or enzyme mixture in an amount of 2 to 50% by weight based on dry matter.

The enzymes are present in the liquid enzyme formulations according to the invention in the form of a so-called aqueous enzyme particle suspension (enzyme slurry). An aqueous enzyme particle suspension of this type is obtained by precipitating the enzymes from the aforementioned enzyme concentrates in a known manner, for example by precipitation processes, spray drying or crystallization, and suspending the resulting precipitate in liquid again, for example the mother liquor or a suitable buffer solution, salt solution or amino acid solution, in a known manner. Suitable precipitation processes by which the enzymes can be precipitated from the enzyme concentrates obtained after the fermentation include, for example, the known processes for precipitating enzymes by the addition of salts, for example by the addition of a concentrated sodium or ammonium sulfate solution, or by the addition of an organic solvent such as, for example, ethanol, acetone, octanol or decanol.

An enzyme crystal suspension (enzyme crystal slurry) is preferably used as the enzyme particle suspension in the liquid enzyme formulations according to the invention. Such a crystal suspension is obtained by adding an aqueous, for example 5 to 20% strength, solution of an alkali metal or alkaline earth metal halide salt to the enzyme concentrate in a known manner, optionally heating to 20° to 35° C., and awaiting the crystallization of the enzyme. An aqueous 10% strength alkali metal chloride solution, in particular a 10% strength sodium chloride solution, is preferably added.

Preferably, an enzyme crystal suspension of a protease, in particular of an alkaline protease such as, for example, Opticlean™ and/or an enzyme crystal suspension of a thermostable amylase such as, for example, Optitherm™, is incorporated into the liquid enzyme formulations according to the invention.

A principal ingredient contained in the liquid enzyme formulations according to the invention is 65 to 95.5% by weight, preferably 80 to 90% by weight, of a liquid alkylene oxide polymer which is based on ethylenediamine and which has a molecular weight in the range from 500 to 8200. Compounds of this type are obtained in a known manner by the addition of alkylene oxide units, for example ethylene oxide or propylene oxide units, onto ethylenediamine. This results in alkylene oxide block polymers or copolymers depending on how the reaction is carried out. Both the alkylene oxide block polymers and the copolymers based on ethylenediamine can be employed in the liquid enzyme formulations according to the invention. The block polymers are preferably used. It is, of course, also possible to use alkylene oxide polymers based on a lower alkylenediamine other than ethylenediamine, for example based on propylenediamine, in the enzyme formulations according to the invention.

The alkylene oxide polymers are employed in liquid form in the enzyme formulations according to the invention. Since the flowability of the alkylene oxide polymers varies depending on the number of alkylene oxide units present in the polymer, the term "liquid" as used herein should be understood to include both low viscosity and high viscosity or pasty alkylene oxide polymers.

The liquid enzyme formulations according to the invention preferably contain an ethylene oxide/propylene oxide polymer based on ethylenediamine. In this case, the molecular weight of this polymer should preferably be in the range from 1500 to 7500. Moreover the ethylene oxide content in a preferred polymer of this type should advantageously be about 40% by weight. Polymers of this type, which contain ethylene oxide and propylene oxide units as block polymers added to ethylenediamine, are commercially available, for example under the proprietary name Synperonic T™ (from ICI).

The liquid enzyme formulations according to the invention furthermore contain from 1 to 10% by weight of a colloidal filler, preferably from 1 to 5% by weight. Suitable colloidal fillers which may be used in the invention include, in particular, highly disperse inorganic compounds selected from the group consisting of silicas, aluminosilicates, aluminas and titanium dioxide. Highly disperse products of this type are generally known and commercially available. Preferably, highly disperse silicas are used. For example, particularly suitable highly disperse silicas are commercially available from Degussa AG under the tradename Aerosil™, such as Aerosil 200™.

One preferred embodiment of a liquid enzyme formulation according to the invention contains 3 to 10% by weight of suspended enzyme crystals of a highly alkaline protease, 5 to 10% by weight water, 1 to 5% by weight of Aerosil™ 200 and 80 to 90% by weight of-Synperonic T304™. The protease activity of a formulation of this type according to the invention may amount to 500,000 to 800,000 DU/g (DU=Delft units). That amount of proteolytic activity which yields an extinction difference (1 cm light path; 275 nm; determined with referenc to a blank sample) of 0.400 after breakdown of casein by 1 ml of 2% strength enzyme solution (w/w) is defined as 1,000 DU.

The invention also relates to a process for preparing liquid enzyme formulations in which 3 to 25% by weight of suspended enzyme particles, optionally 0.5 to 30% by weight of water, 1 to 10% by weight of a colloidal filler and 65 to 95.5% by weight of a liquid alkylene oxide polymer based on ethylenediamine with a molecular weight in the range from 500 to 8200 are mixed together with stirring, where the percentage by weight data are based on the finished complete formulation.

The process is advantageously carried out in such a manner that the liquid alkylene oxide polymer based on ethylenediamine is placed in a vessel and then the colloidal filler is slowly added with vigorous stirring, after which the appropriate enzyme particle suspension, which has been homogenized by stirring, is stirred in. An ethylene oxide/propylene oxide polymer based on ethylenediamine is preferably used. This polymer preferably will have a molecular weight in the range from 1500 to 7500. It is possible to employ for this purpose, for example, a commercially available compound sold under the proprietary name Synperonic™, for example Synperonic T304™, which has a molecular weight of about 1650. In most cases, an appropriate amount of water is added with the enzyme particle suspension because the added enzyme particle suspension also contains water. If desired, any deficiency in the appropriate amount of water can also be made up by adding additional water. An enzyme crystal suspension of a highly alkaline protease whose enzyme activity has been concentrated in a known manner to 2 million to 6 million DU/ml is preferably used as the enzyme particle suspension.

The invention additionally relates to liquid detergents and cleaners which contain the liquid enzyme formulations according to the invention. The liquid enzyme formulations according to the invention are preferably employed in liquid detergents for cleaning textiles or in liquid dishwashing compositions. Besides the liquid enzyme formulations, the detergent or cleaner formulations of the invention may contain conventional amounts of other ingredients and/or adjuvants customarily used in formulating liquid detergents and/or cleaners, for example surfactants, builders and, optionally bleaches or bleach precursors. Suitable adjuvants include, for example, enzyme stabilizers, complexing and chelating agents, foam regulators and additives such as corrosion inhibitors, anti-electrostatic agents, dyes, perfumes, bactericides,'fungicides and activators.

The liquid enzyme formulations according to the invention exhibit surprisingly good properties which are particularly suitable for use in liquid detergent and cleaner formulations. Thus, the liquid enzyme formulations according to the invention have a very high storage stability, with the enzyme activity of the enzymes incorporated in these liquid enzyme formulations remaining virtually unchanged over a long period of time. In addition, the liquid enzyme formulations according to the invention are very sedimentation-stable. Due to their low viscosity, the liquid enzyme formulations according to the invention can easily be metered and are thus can be readily incorporated into liquid detergents or cleaners.

The following examples are intended to illustrate the invention in further detail without limiting its scope.

EXAMPLE 1:

Preparation of a liquid enzyme formulation which contains a highly alkaline protease as enzyme ingredient.

The activity of the protease processed in the liquid enzyme formulations was determined in Delft units (DU). 1000 DU are equivalent to the proteolytic activity which with a volume of 1 ml of 2% strength enzyme solution (w/w) yields an extinction difference (1 cm light path; 275 nm; determination with blank sample as reference) of 0.400 after breakdown of casein.

A *Bacillus alcalophilus* (DSM No. 5466) was fermented in a known manner. Insoluble accompanying substances were removed from the fermenter broth by filtration using filtering aids and flocculants. The pH of the filtrate was adjusted to 5.2, and the protease activity was concentrated by a factor of about 4 to about 750,000 DU/ml by ultrafiltration. After the ultrafiltration, a 10% strength sodium chloride solution was added, the mixture was heated to about 30° C., and the solution was allowed to stand until the enzyme crystallized. An enzyme crystal suspension was obtained and was concentrated in a known manner by removal of the mother liquor to yield a suspension with a protease activity of about 3.6 million DU/ml.

The enzyme crystal suspension of the highly alkaline protease was subsequently processed produce liquid enzyme formulations according to the invention in accordance with the following formula:

5 wt-% suspended enzyme crystals
7.0 wt-% water (introduced with the suspended enzyme crystals)
2.6 wt-% Aerosil 200™ (highly disperse silica)
85.4 wt-% Synperonic T304™ (liquid ethylene oxide/propylene oxide polymer based on ethylenediamine, MW: about 1650).

The liquid enzyme formulations according to the invention were prepared by introducing the stated amount of Synperonic T304™ into a vessel to which the stated amount of Aerosil 200™ was slowly added with vigorous stirring. Subsequently, the enzyme crystal suspension, which had been previously homogenized by stirring, was added with stirring. A sedimentation-stable liquid enzyme formulation of the highly alkaline protease having a protease activity of about 678,000 DU/g was obtained.

EXAMPLE 2:

An enzyme crystal suspension of a protease obtained in a manner analogous to Example 1 was prepared in the same manner in accordance with the following formula:

10 wt-% suspended enzyme crystals
7 wt-% water (introduced with the suspended enzyme crystals)
5.2 wt-% Aerosil 200™
77.8 wt-% Synperonic T304™

A sedimentation-stable liquid enzyme formulation having a protease activity of about 960,000 DU/g was obtained.

EXAMPLE 3:

A liquid enzyme formulation of a protease was prepared as described in Examples 1 and 2 in accordance with the following formula:

25 wt-% suspended enzyme crystals
7.4 wt-% water (introduced with the suspended enzyme crystals)
2.6 wt-% Aerosil 200™
65 wt-% Synperonic T304™

A sedimentation-stable liquid enzyme formulation with a protease activity of about 1.8 million DU/g was obtained.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A liquid enzyme formulation comprising:
3 to 10 wt-% of suspended enzyme particles;
1 to 10 wt-% of a colloidal filler, and
80 to 90 wt-% of a liquid alkylene oxide polymer of ethylenediamine having a molecular weight in the range from 500 to 8200, and
balance water to make 100%.

2. A liquid enzyme formulation according to claim 1, wherein the liquid alklyene oxide polymer has an alkylene oxide content of about 40% by weight.

3. A liquid enzyme formulation according to claim 1, wherein said alkylene oxide polymer is an ethylene oxide/propylene oxide polymer of ethylenediamine.

4. A liquid enzyme formulation according to claim 3, wherein said ethylene oxide/propylene oxide polymer of ethylenediamine has a molecular weight in the range from 1500 to 7500.

5. A liquid enzyme formulation according to claim 1, wherein said suspended enzyme particles comprise at least one enzyme selected from the group consisting of proteases, amylases, lipases, oxidases, oxygenases, cellulases, and hemicellulases.

6. A liquid enzyme formulation according to claim 4, wherein said suspended enzyme particles comprise suspended protease particles.

7. A liquid enzyme formulation according to claim 4, wherein said suspended enzyme particles comprise suspended amylase particles.

8. A liquid enzyme formulation according to claim 1, wherein said enzyme particle suspension is an enzyme crystal suspension.

9. A liquid enzyme formulation according to claim 1, wherein said colloidal filler is colloidal silica.

10. A liquid detergent composition comprising a liquid enzyme formulation according to claim 1, in admixture with at least one detergent ingredient selected from the following surfactants, builders, bleaches, bleach precursors, enzyme stabilizers, complexing agents, chelating agents, foam regulators, corrosion inhibitors, anti-electrostatic agents, dyes, perfumes, bactericides, fungicides and activators.

11. A process for preparing a liquid enzyme formulation comprising admixing
3 to 10 wt-% of suspended enzyme particles;
1 to 10 wt-% of a colloidal filler, and
80 to 90 wt-% of a liquid alkylene oxide polymer of ethylenediamine having a molecular weight in the range from 500 to 8200, and
balance water to make 100%.

12. A process according to claim 11, wherein the liquid alklyene oxide polymer has an alkylene oxide content of about 40% by weight.

* * * * *